US007056667B2

(12) United States Patent
Lee et al.

(10) Patent No.: US 7,056,667 B2
(45) Date of Patent: Jun. 6, 2006

(54) SPATIAL LEARNING AND MEMORY

(75) Inventors: Eminy Hsiao-Yuan Lee, Taipei (TW); Kuen-Jer Tsai, Kaohsiung (TW)

(73) Assignee: Academia Sinica, Taipei (TW)

(*) Notice: Subject to any disclaimer, the term of this patent is extended or adjusted under 35 U.S.C. 154(b) by 588 days.

(21) Appl. No.: 10/103,076

(22) Filed: Mar. 21, 2002

(65) Prior Publication Data
US 2003/0181351 A1 Sep. 25, 2003

(51) Int. Cl.
C12Q 1/68 (2006.01)
G01N 33/53 (2006.01)
(52) U.S. Cl. ............................................. 435/6; 435/7.1
(58) Field of Classification Search .................... 435/6, 435/91.2, 7.1
See application file for complete search history.

(56) References Cited

U.S. PATENT DOCUMENTS 6,326,181 B1 * 12/2001 Lang et al. .................. 435/194

OTHER PUBLICATIONS

D'Hooge, R. et al. 2001. Brain Research Reviews 36:60-90.*
Haynes et al. 1998. Electrophoresis 19:1862-1871.*
Tsai K.J. et al. 2002. Proc Natl Acad Sci USA 99:3990-3995.*
Lindner, M.D. 1994. Journal of Neuroscience 14:2282-2289.*
Mazumder et al., 2003. Trends in Biochemical Sciences 28:91-98.*
Warntges 2002. Pflugers Arch European Journal of Physiology 443:617-624.*
Kourrich 2001. Behavioural Brain Research 120:35-46.*
E. H. Y. Lee, et al. *Protein Synthesis in the Hippocampus Associated with Memory Facilitation by Corticotropin-Releasing Factor in Rats*. Peptides, vol. 13, pp. 927-937, 1992.
V. F. Castellucci, et al. *A Quantiative Analysis of 2-D Gels Identifies Proteins in Which Labeling Is Increased Following Long-Term Sensitization in Aplysia*. Neuron, vol. 1, pp. 321-328, Jun. 1998.
Tim Tully. *Discovery of genes involved with learning and memory: An experimental synthesis of Hirschian and Benserian perspectives*. Proc. Natl. Acad. Sci. USA, vol. 93, pp. 13460-13467, Nov. 1996.
N. Popov, et al. *Changes in the incorporation of [$^3$H] Fucose into rat hippocampus after acquisition of a brightness discrimination reaction. An electrophoretic study*. Neuroscience, vol. 5, pp. 161-167, 1980.
A.-Min Huang, et al. *Identification of a novel glial fibrillary acidic protein mRNA isotype related to memory retention in rats*. NeuroReport, vol. 8, pp. 1619-1624, 1997.

A.-Min Huang, et al. *Expression of Integrin-Associated Protein Gene Associated with Memory Formation in Rats*. The Journal of Neuroscience, vol. 18, No. 11, pp. 4305-4313, Jun. 1, 1988.
Hui P. Chang, et al. *Impaired Memory Retention and Decreased Long-Term Potentation in Integrin-Associated Protein-Deficient Mice*. Learning & Memory, vol. 6, pp. 448-457, 1999.
R. G. M. Morris, et al. *Place navigation impaired in rats with hippocampal legions*. Nature, vol. 297, Jun. 24, 1982, pp. 681-683.
May-Britt Moser, et al. *Spatial learning with a minislab in the dorsal hippocampus*. Proc. Natl. Acad. Sci. USA, vol. 92, pp. 9697-9701, Oct. 1995.
Bassima Abdallah, et al. *A Powerful Nonviral Vector for In Vivo Gene Transfer into the Adult Mammalian Brain: Polyethylenimine*. Human Gene Therapy, vol. 7, pp. 1947-1954, Oct. 1996.
K. Imaizumi, et al. *Differential expression of sgk mRNA, a member of the Ser/Thr protein kinase gene gamily, in rat brain after CNS injury*. Molecular Brain Research, vol. 26, pp. 189-196, 1994.
R. D. Hollister, et al. *Distribution of the messenger RNA for the extracellularly regulated kinases 1, 2, and 3, in rat brain: Effects of excitotoxin hippocampal lesions*. Neuroscience, vol. 79, No. 4, pp. 1111-1119, 1997.
Jongsun Park, et al. *Serum and glucocorticoid-inducible kinase (SGK) is a target of the PI 3-kinase-stimulated singaling pathway*. The EMBO Journal, vol. 18, No. 11, pp. 3024-3033, 1999.
Melanie K. Webster, et al. *Characterization of sgk, a Novel Member of the Serine/Threonine Protein Kinase Gene Family Which Is Transcriptionally Induced by Glucocorticoids and Serum*. Molecular and Cellular Biology, vol. 13, No. 4, Apr. 1993, pp. 2031-2040.
Aniko Naray-Fejes-Toth, et al. *SGK is a primary glucocorticoid-induced gene in the human*. Journal of Steroid Biochemistry & Molecular Biology, vol. 75, pp. 51-56, 2000.

(Continued)

*Primary Examiner*—Robert C. Hayes
*Assistant Examiner*—Daniel E. Kolker
(74) *Attorney, Agent, or Firm*—Fish & Richardson P.C.

(57) ABSTRACT

A method of determining whether a patient is deficient in spatial learning and memory. The method includes providing a sample from the patient, the sample containing an sgk gene product; and determining an sgk expression level in the sample. If the sgk expression level in the sample is lower than that in a sample from a normal person, it indicates that the patient is deficient in spatial learning and memory. Also disclosed are a method of identifying a compound for treating deficiency in spatial learning and memory and a method of treating such deficiency.

8 Claims, No Drawings

OTHER PUBLICATIONS

Aniko Naray-Fejes Toth, et al. *sgk Is an Aldosterone-induced Kinase in the Renal Collecting Duct*. The Journal of Biological Chemistry, col. 274, No. 24, pp. 16973-16978, 1999.

David Pearce, et al. *Role of SGK in mineralocorticoid-regulated sodium transport*. Kidney International, vol. 57, pp. 1283-1289, 2000.

Siegfried Waldegger, et al. *Cloning and characterization of a putative human serine/threonine protein kinase transcriptionally modified during anisotonic and isotonic alterations of cell volume*. Proc. Natl. Acad. Sci. USA, vol. 94, pp. 4440-4445, Apr. 1997.

Laurie M. Delmolino, et al. *Heparin Suppresses sgk, an Early Response Gene in Proliferating Vascular Smooth Muscle Cells*. Journal of Cellular Physiology, vol. 173, pp. 371-379, 1997.

Elsa Lee, et al. *Tissue-specific expression of the transcriptionally regulated serum and glucocorticoid-inducible protein kinase (Sgk) during mouse embryogenesis*. Mechanisms in Development, vol. 103, pp. 177-181, 2001.

David S. Olton, et al. *Spatial Correlates of Hippocampal Unit Activity*. Experimental Neurology, vol. 58, pp. 387-409, 1978.

B. L. McNaughton, et al. *The Contributions of Position, Direction and Velocity to Single Unit Activity in the Hippocampus of Freely-moving Rats*. Exp. Brain. Res. vol. 52, pp. 41-49, 1983.

Elizabeth Gould, et al. *Learning enhances adult neurogenesis in the hippocampal formation*. Nature Neuroscience, vol. 2, No. 3, pp. 260-265, 1999.

Edvard Moser, et al. *Spatial Learning Impairment Parallels the Magnitude of Dorsal Hippocampal Lesions, but Is Hardly Present following Ventral Lesions*. The Journal of Neuroscience, vol. 13, No. 9, pp. 3916-3925, 1993.

D. M. Bannerman, et al. *Distinct components of spatial learning revealed by prior training and NMDA receptor blockade*. Nature, vol. 378, pp. 182-186, Nov. 1995.

May-Britt Moser, et al. *Pretraining and the Function of Hippocampal Long-Term Potentiation*. Neuron, vol. 26, pp. 559-561, Jun. 2000.

Carmen Sandi. *The Role and Mechanism of Action of Glucocorticoid Involvement in Memory Storage*. Neural Plasticity, vol. 6, No. 3, pp. 41-52, 1998.

Benno Roosendaal. *Glucocorticoids and the regulation of memory consolidation*. Psychoneuroendocrinology, vol. 25, pp. 213-238, 2000.

Melly S. Oitzl, et al. *Selective Corticosteroid Antagonists Modulate Specific Aspects of Spatial Orientation Learning*. Behavioral Neuroscience, vol. 106, No. 1, pp. 62-71, 1992.

Benno Roosendaal, et al. *Basolateral Amygdala Lesions Block Glucocorticoid-Induced Modulation of Memory for Spatial Learning*. Behavioral Neuroscience, col. 110, No. 5, pp. 1074-1083, 1996.

Melly S. Oitzl, et al. *Spatial Learning Deficits in Mice with a Targeted Glucocorticoid Receptor Gene Disruption*. European Journal of Neuroscience, vol. 9, pp. 2284-2296, 1997.

Melly S. Oitzl, et al. *Point Mutation in the mouse glucocorticoid receptor preventing DNA binding impairs spatial memory*. PNAS, vol. 98, No. 22, pp. 12790-12795, Oct. 2001.

J. M. H. M. Reul, et al. *Two Receptor Systems for Corticosterone in Rat Brain: Microdistribution and Differential Occupation*. Endocrinology, vol. 117, No. 6, pp. 2505-2511, 1985.

Bas van Steensel, et al. *Partial colocalization of glucocorticoid and mineralocorticoid receptors in discrete compartments in nuclei of rat hippocampus neurons*. Journal of Cell Science, vol. 109, pp. 787-792, 1996.

Masafumi Morimoto, et al. *Distribution of glucocorticoid receptor immunoreactivity and mRNA in the rat brain: an immunohistochemical and in situ hybridization study*. Neuroscience Research, vol. 26, pp. 235-269, 1996.

E. Ron de Kloet, et al. *Stress and cognition: are corticosteroids good or bad guys?* TINS, vol. 22, No. 10, pp. 1999.

Francine E. Brennan, et al. *Rapid upregulation of serum and glucocorticoid-regulated kinase (sgk) gene expression by corticosteroids in vivo*. Molecular and Cellular Endocrinology, vol. 166, pp. 129-136, 2000.

Melly S. Oitzl, et al. *Continuous blockade of brain glucocorticoid receptors facilitates spatial learning and memory in rats*. European Journal of Neuroscience, vol. 10, pp. 3759-3766, 1998.

Constantine Pavlides, et al. *Role of adrenal steroid mineralocorticoid and glucocorticoid receptors in long-term potentiation in the CA 1 field of hippocampal slices*. Brain Research, vol. 728, pp. 229-235, 1996.

\* cited by examiner

SPATIAL LEARNING AND MEMORY

BACKGROUND

Memory formation requires de novo RNA and protein synthesis. Inhibition of mRNA and protein synthesis impairs memory formation in various behavioral task performances by rats. Such observations suggest that neural activities associated with learning lead to the expression of various genes encoding proteins that play important roles in memory formation (Davis and Squire (1984) Psychol. Bull. 96, 518–559; Matthies (1989) Annu. Rev. Psychol. 40, 381–404; and Lee, et al. (1992) Peptides 13, 927–937).

Extensive efforts have been made to identify genes specifically associated with certain forms of learning and memory. For example, by using two-dimensional gel analysis, several candidate proteins have been identified to be related to long-term sensitization of the gill-withdrawal reflex in Aplysia (Castellucci, et al. (1988) Neuron 1, 32 1–328). Approximately ten Drosophila genes have been found to be associated with olfactory learning and memory by screening of Drosophila mutants (Tully (1996) Proc. Nati. Acad. Sci. USA 93, 13460–13467). Further, by using a double-labeling method, proteins with increased glycosylation as a result of training have been identified in rats (Popov, et al. (1980) Neuroscience 5, 161–167).

SUMMARY

This invention relates to the use of a serum- and glucocorticoid-inducible kinase (sgk) gene in diagnosing and treating spatial learning and memory deficiency, and in identifying therapeutic compounds for treating such deficiency.

"Spatial learning and memory" is the ability to gain and retain knowledge of a concept or an object relating to, occupying, or having the character of space and orientation from study, instruction, or experience.

In one aspect, this invention features a method of determining whether a patient is deficient in spatial learning and memory. The method includes providing a sample containing an sgk gene product from a patient and determining an sgk expression level in the sample. If the sgk expression level in the sample is lower than that in a sample from a normal person, the patient is deficient in spatial learning and memory. The sample can be prepared from a brain biopsy, e.g., a cerebrospinal fluid. The sgk gene product can be either an mRNA encoding an SGK protein, or an SGK protein itself. The sgk mRNA level can be determined, for example, by in situ hybridization, PCR, or Northern blot analysis. The SGK protein level can be determined, for example, by Western blot analysis.

In another aspect, this invention features a method of identifying a compound for treating deficiency in spatial learning and memory. The method includes contacting a compound with a cell (e.g., a neural cell) expressing an sgk gene, and then determining an sgk expression level in the cell. If the sgk expression level in the presence of the compound is higher than that in the absence of the compound, the compound is a drug candidate for treating deficiency in spatial learning and memory.

Also within the scope of this invention is a method of treating deficiency in spatial learning and memory. The method includes identifying a patient suffering from deficiency in spatial learning and memory and administering to the patient a composition to increase an SGK level in the patient. The composition may contain a nucleic acid encoding an SGK protein, or an SGK protein itself. The "SGK protein" refers to both the wild-type SGK protein and its variants with an equivalent biological function (e.g., a fragment of the wild-type SGK protein). The composition can be administered directly to the brain of a patient in the dorsal hippocampus such as the dentate gyrus or the pyramidal layer (e.g., the CA1 or CA3 area).

The present invention provides methods for diagnosing and treating spatial learning and memory deficiency associated with insufficient expression of the sgk gene. The details of one or more embodiments of the invention are set forth in the accompanying description below. Other features, objects, and advantages of the invention will be apparent from the detailed description, and from the claims.

DETAILED DESCRIPTION

The sgk gene was originally identified as a member of the serine/threonine protein kinase gene family that is transcriptionally induced by glucocorticoid and serum (Webster, et al. (1993) Mol. Cell. Biol. 13, 2031–2040). It is also known as a primary glucocorticoid-induced gene in several human cell lines (Naray-Fejes-Toth, et al. (2000) J. Steroid Biochem. Mol. Biol. 75, 51–56). Sgk has been demonstrated to mediate the early phase of the stimulatory effect of aldosterone on sodium re-absorption in renal epithelia (Naray-Fejes-Toth, et al. (1999) J. Biol. Chem. 274, 16973–16978; and Pearce, et al. (2000) Kidney Inter. 57, 1283–1289) and be associated with the proliferation of vascular smooth muscle cells (Delmolino and Castellot (1997) J. Cell. Physiol. 173, 371–379). The expression of sgk mRNA is sensitive to anisotonic and isotonic alterations of a cell, suggesting that it is involved in the regulation of cell volume (Waldegger, et al. (1997) Proc. Natl. Acad. Sci. USA 94, 4440–4445).

Sgk has also been shown to play a role in the central nervous system. The sgk mRNA level increases at the lesion site after brain injury, suggesting that sgk is probably involved in axonal regeneration (Imaizumi, et al. (1994) Mol. Brain Res. 26, 189–196). Further, sgk expression is transcriptionally regulated and shows a tissue- and stage-specific pattern during embryogenesis and postnatal development (Imaizumi, et al. (1994) Mol. Brain Res. 26, 189–196; and Lee, et al. (2001) Mech. Dev. 103, 177–181).

The present invention is based on an unexpected discovery that sgk plays an important role in spatial learning and memory. As demonstrated in the example below, hippocampal sgk mRNA level is approximately four-fold higher in fast learner rats than that in slow learner rats. More specifically, significant higher sgk mRNA levels are found in CA1, CA3 of the pyramidal layer and in the dentate gyrus of a brain in fast learner rats. In addition, transient transfection of a wild-type sgk DNA to CA1 enhances spatial learning and memory in rats. In contrast, transient transfection of a dominant negative sgk mutant DNA to CA1 impaires spatial learning and memory in rats.

This invention provides methods for diagnosing and treating spatial learning and memory deficiency associated with insufficient expression of the sgk gene, and identifying therapeutic compounds for treating such deficiency.

A diagnostic method of this invention involves comparing an sgk expression level in a sample (e.g. a brain biopsy such as a cerebrospinal fluid) prepared from a patient with that in a sample prepared from a normal person, i.e., a person who does not suffer from spatial learning and memory deficiency. A lower sgk expression level indicates that the patient is deficient in spatial learning and memory. The methods of this invention can be used on their own or in conjunction with other procedures to diagnose spatial learning and memory deficiency in appropriate subjects.

The sgk expression level can be determined at either the mRNA level or at the protein level. Methods of measuring mRNA levels in a tissue sample or a body fluid are known in the art. In order to measure mRNA levels, cells can be lysed and the levels of sgk mRNA in the lysates or in RNA purified or semi-purified from the lysates can be determined by any of a variety of methods including, without limitation, hybridization assays using detectably labeled sgk-specific DNA or RNA probes and quantitative or semi-quantitative RT-PCR methodologies using appropriate sgk-specific oligonucleotide primers. Alternatively, quantitative or semi-quantitative in situ hybridization assays can be carried out using, for example, tissue sections or unlysed cell suspensions, and detectably (e.g., fluorescently or enzyme) labeled DNA or RNA probes (see the example below). Additional methods for quantifying mRNA include RNA protection assay (RPA) and SAGE.

Methods of measuring protein levels in a tissue sample or a body fluid are also known in the art. Many such methods employ antibodies (e.g., monoclonal or polyclonal antibodies) that bind specifically to an SGK protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) familiar to those in the art can be used to enhance the sensitivity of the methodologies. Some of these protein-measuring assays (e.g., ELISA or Western blot) can be applied to bodily fluids or to lysates of cells, and others (e.g., immunohistological methods or fluorescence flow cytometry) applied to histological sections or unlysed cell suspensions. Methods of measuring the amount of label will be depend on the nature of the label and are well known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

This invention also provides a method for identifying candidate compounds (e.g., proteins, peptides, peptidomimetics, peptoids, antibodies, small molecules or other drugs) that increase the sgk expression level in a cell (e.g., a neural cell). Compounds thus identified can be used to treat conditions characterized by insufficient SGK activity, e.g., spatial learning and memory deficiency.

The candidate compounds of the present invention can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann, et al. (1994) J. Med. Chem. 37, 2678–85; and Lam (1997) Anticancer Drug Des. 12, 145.

Examples of methods for the synthesis of molecular libraries can be found in the art, for example, in: DeWitt, et al. (1993) PNAS USA 90, 6909; Erb, et al. (1994) PNAS USA 91, 11422; Zuckermann, et al. (1994) J. Med. Chem. 37, 2678; Cho, et al. (1993) Science 261, 1303; Carrell, et al. (1994) Angew. Chem. Int. Ed. Engl. 33, 2059; Carell, et al. (1994) Angew. Chem. Int. Ed. Engl. 33, 2061; and Gallop, et al. (1994) J. Med. Chem. 37, 1233.

Libraries of compounds may be presented in solution (e.g., Houghten (1992) Biotechniques 13, 412–421), or on beads (Lam (1991) Nature 354, 82–84), chips (Fodor (1993) Nature 364, 555–556), bacteria (Ladner, U.S. Pat. No. 5,223,409), spores (Ladner U.S. Pat. No. 5,223,409), plasmids (Cull, et al. (1992) PNAS USA 89, 1865–1869), or phages (Scott and Smith (1990) Science 249, 386–390; Devlin (1990) Science 249, 404–406; Cwirla, et al. (1990) PNAS USA 87, 6378–6382; Felici (1991) J. Mol. Biol. 222, 301–310; and Ladner supra.).

To identify compounds that increase the sgk expression level in a cell, a cell (e.g., a neural cell) expressing the sgk gene is contacted with a candidate compound and the expression level of the sgk gene is evaluated relative to that in the absence of the candidate compound. The cell can be a cell that naturally expresses sgk, or a cell that is modified to express a recombinant nucleic acid, for example, having the sgk promoter fused to a marker gene. The level of the sgk gene expression or the marker gene expression can be determined by methods described above. When the expression level of the sgk gene or the marker gene is greater in the presence of the candidate compound than that in the absence of the candidate compound, the candidate compound is identified as a potential drug for treating spatial learning and memory deficiency.

This invention also provides a method for treating spatial learning and memory deficiency. Patients to be treated can be identified, for example, by determining the sgk gene expression level in a sample prepared from a patient by methods described above. If the sgk gene expression level is lower in the sample from the patient than that in a sample from a normal person, the patient is a candidate for treatment with an effective amount of compound that increases the SGK level in the patient.

The treatment method can be performed in vivo or ex vivo, alone or in conjunction with other drugs or therapy.

In one in vivo approach, a therapeutic compound (e.g., a compound that increases the sgk expression level in a cell or an SGK protein) itself is administered to the subject. Generally, the compound will be suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. For treatment of spatial learning and memory deficiency, the compound can be delivered directly to the dorsal hippocampus (e.g., the dentate gyrus or the pyramidal layer such as the CA1 or CA3 area).

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01–100.0 μg/kg. Wide variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an SGK protein can be delivered to the subject, for example, by the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al. (1995) J. Mol. Med. 73, 479). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the SGK protein is operatively linked to a promoter or enhancer-promoter combination. Enhancers provide expression specificity in terms of time, location, and level. Unlike a promoter, an enhancer can function when located at variable distances from the transcription initiation site, provided a promoter is present. An enhancer can also be located downstream of the transcription initiation site.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., an increased SGK level) in a treated patient. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to $10^{12}$ copies of the polynucleotide molecule. This dose can be repeatedly administered, as needed. Routes of administration can be any of those listed above.

An ex vivo strategy for treating patients with spatial learning and memory deficiency can involve transfecting or transducing cells obtained from the subject with a polynucleotide encoding an SGK protein. Alternatively, a cell can be transfected in vitro with a vector designed to insert, by homologous recombination, a new, active promoter upstream of the transcription start site of the naturally occurring endogenous sgk gene in the cell's genome. Such methods, which "switch on" an otherwise largely silent gene, are well known in the art. After selection and expansion of a cell that expresses SGK at a desired level, the transfected or transduced cells are then returned to the subject. The cells can be any of a wide range of types including, without limitation, neral cells, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the SGK protein for as long as they survive in the subject.

The ex vivo methods include the steps of harvesting cells from a subject, culturing the cells, transducing them with an expression vector, and maintaining the cells under conditions suitable for expression of the sgk gene. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the sgk gene. The cells may then be injected or implanted into the patient.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications recited herein are hereby incorporated by reference in their entirety.

Materials and Methods

1. Animals

Adult male Sprague-Dawley rats bred at the Animal Facility of the Institute of Biomedical Sciences, Academia Sinica, Taiwan were used in the present study. Animals were housed in a room maintained on a 12/12 hr light/dark cycle (light on at 6:30 AM) with food and water continuously available. Experimental procedures follow the Guidelines of Animal Use and Care of NIH.

2. Water Maze and Spatial Learning Procedures

The water maze used was a plastic circular pool, 2.0 m in diameter and 0.6 m in height, filled with water ($25\pm2°$ C.) to a depth of 20 cm. A circular platform (8 cm in diameter) was placed at a specific location away from the edge of the pool. The top of the platform was submerged 1.5 cm below the water surface. Water was made cloudy by addition of milk powder. Distinctive visual cues were set on the wall.

For spatial learning, animals were subjected to four trials a session, two sessions a day with one given in the morning and the other given in the afternoon. Eight sessions were given to screen for the fast and slow learners, and four sessions were given two days after sgk DNA transfection, as transient DNA transfection has been shown to have an optimal efficiency between 48 and 72 hr after injection (Abdallah, et al. (1996) Human Gene Ther. 7, 1947–1954).

In each of the four trials, animals were placed at four different starting positions equally spaced around the perimeter of the pool in a random order. Animals were allowed to find the platform in 120 sec. If an animal cannot find the platform in 120 sec, it is guided to the platform. After mounting the platform, animals were allowed to stay there for 20 sec. The time each animal spent to reach the platform was recorded as the escape latency.

114 rats were screened for fast and slow learners. The rats who found the hidden platform within 30 sec before the end of the third session were assigned as fast learners (i.e., fewer trials were needed for memory consolidation). The rats who did not find the platform within 30 sec until session 7 or 8 were assigned as slow learners (i.e., more trials were needed for memory consolidation). The rats that fell in between were assigned as controls. Among the 114 rats screened, 21 rats were assigned as fast learners and 21 rats were assigned as slow learners. The remaining 72 rats were assigned as controls.

In a visible platform experiment, a flag was mounted on the platform and was 2.5 cm above the water surface. In addition, milk powder was not added to the swimming pool so that the rats could visualize the location of the platform.

3. Differential Display-PCR

Differential display-PCR was performed as previously described (Huang, et al. (1998) J. Neurosci. 18, 4305–4313) with slight modifications. Random primers (RNAimage™ Kit) were purchased from GenHunter Corporation (TN, USA). Briefly, three separate reaction mixtures were prepared, each containing 2 µl of 2 µM one-base-anchored primers (H-T$_{11}$A, H-T$_{11}$C and H-T$_{11}$G) for reverse transcription (RT). Each of the three primers were mixed with 2 µl of 0.1 µg/µl total RNA, 1.6 µl of 250 µM dNTP, 4 µl of 5×RT buffer and 9.4 µl of DEPC H$_2$O final volume of 19 µl, and incubated at 65° C. for 5 min and then at 37° C. for 10 min. One microliter of MMLV reverse transcriptase (100 U/µl) (Life Technologies/BRL, USA) was added to the mixture and incubated for another 50 min at 37° C. The reaction was terminated by heating the sample at 75° C. for 5 min.

After RT, the reverse-transcribed products were aliquoted into fresh tubes and amplified with 80 different arbitrary primers (H-AP1~H-AP80). For each amplification, two microliters of the RT product were added to a PCR reaction mixture containing 2 µl of 2 µM H-AP primer, 2 µl of 2 µM H-T$_{11}$M primer (M may be A, C or G), 1.6 µl of 25 µM dNTP, 2 µl of 10×PCR buffer, 1 µl of α-[$^{35}$S]dATP (1000 Ci/mmole) (Amersham, UK), 1 U of Taq DNA polymerase (Perkin-Elmer, USA) and 9.2 µl dH$_2$O to a total volume of 20 µl. The PCR parameters used were 40 cycles of 94° C. for 30 sec, 40° C. for 2 min and 72° C. for 30 sec, followed by 72° C. for 5 min. All 240 reactions were performed in duplicate. The amplified cDNA fragments were recovered from sequencing gels and cloned into the PCR 2.1 TA vector (Invitrogen, USA).

4. Northern Blot

Total RNA was fractioned by electrophoresis through 1.0% agarose/formaldehyde gels, transferred overnight onto Hybond™-XL (Amersham) in 20×SSC, and fixed to the membrane by exposure to UV irradiation. The membrane was pre-hybridized for 4 hr at 65° C. in a hybridization buffer containing 6×SSC, 5× Denhardt's solution (0.5% Ficoll, 0.5% polyvinylpyrrolidone, 0.5% BSA), 0.5% sodium dodecyl sulfate (SDS) and 100 µg/ml of heat-denatured salmon sperm DNA. The membrane was then hybridized overnight at 65° C. in the hybridization buffer with 5 ng/ml $^{32}$P-labeled cDNA probe.

A 608 bp sgk cDNA probe was used to hybridize to a single mRNA species of about 2.5 kb (Imaizumi, et al. (1994) Mol. Brain Res. 26, 189–196). The rat GAPDH cDNA probe that hybridizes to a 1.3 kb mRNA species was used as an internal control. After two washes in 2×SSC/0.1% SDS at 42° C. for 10 min, followed by two washes at 65° C. for 10 min in 0.1×SSC/0.1% SDS, the membrane was dried and autoradiographed.

5. In Situ Hybridization

In situ hybridization was performed using a 45-base anti-sense probe (5'-GCG GAG ATC CCT CTT AGA CCT GCA TCT TCC TTC TCA CTG AGA CCA-3'; SEQ ID NO:1) and a control sense probe (5'-TGG TCT CAG TGA GAA GGA AGA TGC AGG TCT AAG AGG GAT CTC CGC-3'; SEQ ID NO:2) (Hollister, et al. (1997) Neuroscience 79, 1111–1119). Both probes were synthesized and purified by Sigma Genosys (Texas, USA). The probes (15 pmol/µl) were 3' end-labeled by incubating at 37° C. for 15 min with α-[$^{35}$S]dATP and terminal deoxynucleotidyl transferase (25 U, Boehringer Mannheim, USA).

Tissue samples were rinsed with 20×SSC for 10 min at room temperature prior to hybridization. The labeled sgk oligonucleotide probes (1×10$^6$ cpm/slide) in 100 µg/ml yeast transfer RNA, 500 µg/ml salmon sperm DNA, and Denhardt's solution were applied to each slide. Slides were covered with cover-slips and sealed with parafilm. The hybridization proceeded at 42° C. for 24 hr. Cover-slips were removed, and slides were rinsed with 2×SSC and then with 1×SSC containing 1.0 M DTT (0.1%), followed by 30 min wash with 0.5×SSC containing 1.0 M DTT at 47° C. A final wash with 0.5×SSC containing 1.0 M DTT was performed at room temperature for 30 min. Slides were dehydrated through a series of ethanol baths (50%, 75%, 95% and 100%) and exposed to Hyperfilm MP (Amersham Biosciences Asia Pacific, Hong Kong) for two weeks. Signals from in situ hybridization were quantified by measuring the optic density of the relevant fields using the National Institute of Health IMAGE Program.

6. Plasmid Construction and DNA/PEI Complexes Preparation

For construction of the hemagglutinin (HA) epitope-tagged plasmid (HA-SGK), full length sgk gene was cloned by amplifying the rat hippocampal sgk cDNA with primers 5'-CGG AAT TCA CCG TCA AAA CCG AGG CTC G-3' (SEQ ID NO:3) and 5'-GCT CTA GAT CAG AGG AAG GAG TCC ATA GG-3' (SEQ ID NO:4). The PCR product was subcloned between the EcoRI and XbaI sites of the mammalian expression vector pcDNA3-HA. The Ser422mutant (kinase-deficient HA-SGK S422A; Park, et al. (1999) EMBO J. 18, 3024–3033) was generated by PCR using primers 5'-CGG AAT TCA CCG TCA AAA CCG AGG CTC G-3' (SEQ ID NO:5) and 5'-GCT CTA GAT CAG AGG AAG GAG TCC ATA GGA GGG GCA TAG GCG AAG-3' (SEQ ID NO:6) with HA-SGK as a template and inserted into the pcDNA3-HA expression vector. The efficiency of mutant sgk DNA transfection was confirmed by decreased sgk activity in HEK 293 cells (Park, et al. (1999) EMBO J. 18, 3024–3033).

Before injection, plasmid DNA was diluted with 5% glucose to a concentration of 5 µg/µl. Linearized polyethylenimine (PEI) of 22 kDa (Sigma, USA) was diluted to 0.1 M with 5% glucose and was added to the DNA solution. The mixture was vortexed for 30 sec and allowed to equilibrate at room temperature for 10 min before injection.

7. Intra-Hippocampal DNA Transfection

Rats were anesthetized with pentobarbital (40 mg/kg, ip) and subjected to stereotaxic surgery. Two 23 gauge stainless steel thin-wall cannulae were implanted bilaterally to the CA1 area at the following coordinates: 3.5 mm posterior to the bregma, 2.5 mm lateral to the midline, and 3.4 mm ventral to the skull surface.

After recovery from the surgery, 1 µl of 5% glucose solution containing 2 µg plasmid DNA complexed with 10 PEI equivalents (Abdallah, et al. (1996) Human Gene Ther. 7, 1947–1954) were injected to the CA1 area (0.5 µl/min). The injection needle was left in place for 5 min to limit the diffusion of the injected DNA.

Rats were subjected to the spatial learning task 48 hr later. The area of transfection in CA1 was then examined and quantified by using the NIH IMAGE Program according to the criterion of Amaral and Witter (Amaral and Witter (1995) in The Rat Nervous System, 2nd ed., ed. Paxinos, G. (Academia Press), pp. 443–493).

8. Immunohistochemistry

Brain sections were rinsed with 1×PBS for 10 min at room temperature and permeablized with cold EtOH/CH$_3$COOH (95%:5%) for 10 min, followed by three times of 1×PBS for 10 min. The sections were pre-incubated in a blocking solution containing 3% normal goat serum, 3% BSA and 0.2% Triton X-100 in 1×PBS for 2 hr at room temperature, followed by three times of 1×PBS for 10 min.

For immunofluorescence analysis, tissue sections were incubated with a mouse monoclonal anti-HA antibody (Boehringer Manrheim, dilution 1:100) in a blocking buffer at 4° C. overnight. Sections were washed three times with 1×PBS and incubated with a secondary antibody, goat anti-mouse FITC-conjugated IgG antibody (Sigma, dilution 1:100), in 1×PBS for 1 hr at room temperature. Sections were washed three times with 1×PBS and mounted with a mounting medium.

9. Quantitative RT-PCR

RT reactions were performed as described above. Rat hypoxanthine phosphoribosyl transferase (HPRT) mRNA was used as an internal control template. Synthetic primers 5'-CTC TGT GTG CTG AAG GGG GG-3' (SEQ ID NO:7) and 5'-GGG ACG GAG CAA GAG ACA TT-3' (SEQ ID NO:8) were used to amplify the HPRT mRNA to generate a PCR product of 625 bp in length. Synthetic primers 5'-TTT TTT TTC CCA ACC CTT GC-3' (SEQ ID NO:9) and 5'-AAT GAA CAA AGG TTG GGG GG-3' (SEQ ID NO:10) were used to amplify the sgk mRNA to generate a PCR product of 390 bp in length. The PCR parameters used were: 26 cycles of 94°C. for 30 sec, 57°C. for 30 sec, 72°C. for 40 sec, followed by a final elongation at 72°C. for 7 min. The PCR product was analyzed on a native 8.0% polyacrylamide gel and autoradiographed for phosphoimage analysis (Molecular Dynamics, USA).

Results

1. Differential Display-PCR

Three fast learners and three slow learners were randomly chosen among the 21 rats in each group. Total RNA was extracted from the dorsal hippocampus and was subjected to differential display-PCR analysis. Other fast learners and slow learners were subjected to Northern blot analysis, in situ hybridization and spatial learning test with visible platform, respectively.

Approximately 15,000 DNA fragments were generated by differential display-PCR, among which 98 correspond to mRNA molecules consistently and differentially expressed in fast and slow learners based on an "all-or-none" criterion (i.e., a cDNA band is seen or not seen on a gel). Further cloning and sequencing analyses revealed that 41 of them represent unknown genes, 52 of them represent mitochondrial genes, 2 of them represent genes encoding transmembrane proteins, another 2 of them represent genes encoding intracellular proteins, and the last one represents a gene encoding a nuclear protein. When the primer set H-AP48 (a 5'primer with an oligonucleotide sequence of 5'-AAGCTTGCGGTGA-3'; SEQ ID NO:11) and H-T$_{11}$A (a 3' primer with an oligonucleotide sequence of 5'-AAGCTTTTTTTTTTTA-3'; SEQ ID NO:12) were used, a cDNA fragment (402 bp in length) generated was found to have 96% sequence homology to the 3'-end region of the rat sgk gene. The expression level of this gene was much higher in the dorsal hippocampus of fast learners than in that of slow learners.

2. Northern Blot Analysis

Northern blot experiment was carried out for seven fast learners and seven slow learners to confirm the results obtained from differential display-PCR. Statistical analysis revealed that the sgk mRNA level was approximately four-fold higher in the dorsal hippocampus of fast learners than in that of slow learners [t(1,12)=8.01, P=0.01].

3. In Situ Hybridization

In situ hybridization analyses of three fast learners and three slow learners revealed that the sgk mRNA was mainly expressed in the dentate gyrus of hippocampus in slow learners, although the distribution of sgk mRNA in the pyramidal cell layer could also be visualized. In contrast, high levels of sgk mRNA were observed in both the pyramidal cell layer and dentate gyrus of the hippocampus in fast learners. Further analyses revealed that the sgk mRNA level was markedly higher in CA1, CA3 and the dentate gyrus [t(1,4)=33.85, 39.37 and 63.83, respectively, all P<0.01] in fast learners. No specific signal was observed when the sense probe was used as a control probe.

4. Effects of sgk DNA Transfection on Water Maze Performance by Rats

Effects of sgk DNA transfection on water maze performance by rats were examined in order to elucidate the cause-effect relationship between sgk expression and memory consolidation. It was found that sgk DNA transfection significantly affected spatial learning in rats [F (2,21)=17.06, P<0.001]. Further analyses revealed that mutant sgk DNA transfection to CA1 significantly impaired spatial learning performance [F(2,21)=6.9, P<0.05]. In contrast, wild-type sgk DNA transfection markedly enhanced spatial learning performance by rats [F(2,21)=10.32, P<0.05]. The first trial performance was not markedly different [F(2,21)=1.00, P>0.05].

Immunohistochemistry experiments using a first antibody against HA and an FITC-conjugated IgG secondary antibody were conducted in order to confirm the efficiency of sgk DNA transfection. No fluorescent signal was observed when a non-HA vector was transfected. In contrast, when the HA-SGK S422A mutant DNA was transfected into the CA1 area, fluorescent signal was clearly visible. At a higher magnification, it was found that the DNA construct was indeed transfected into neurons in the CA1 area. The averaged area of transfection in CA1 was approximately 22.4% for the SGK S422A group (22.4±2.2) and 23.1% for the SGKWT group (23.1±1.8).

5. Sgk mRNA Expression is Induced during Learning

To find out whether sgk mRNA expression is induced during learning or is constitutively higher in fast learners, quantitative RT-PCR was used to analyze the sgk mRNA level in ten randomly chosen naïve rats. Since both total RNA (25, 50, 75 and 100 ng) and the PCR cycle number (24, 26, 28 and 30) were found to have a linear relationship with the optical densities of sgk and HPRT cDNA bands produced, 50 ng total RNA and 26 cycles were used in this experiment. The results revealed that hippocampal sgk mRNA levels only differed by approximately 0%–37% among individual naive rats.

6. Water Maze Performance with Visible Platform by Fast Learners, Slow Learners, and Sgk DNA Transfected Rats A visible platform was included in the water maze performance test to find out whether visual discrimination ability, motor coordination and motivational state are different between fast learners and slow learners and therefore contribute to the difference in the water maze performance.

Different batches of fast learners (n=8) and slow learners (n=8) were subjected to the same water maze learning task with a visual cue (e.g., a flag) attached to the platform. Both the fast learners and slow learners reached the platform successfully during trials in the first session. Statistical analysis indicated that there was not a significant difference in water maze performance between these two groups of rats for the entire session [$F(1,14)=0.34$, $P>0.05$] and for the first trial only [$F(1,14)=3.03$, $P>0.05$].

Whether sgk is involved in sensory and motor functions and therefore affects spatial learning was also examined. Results revealed that rats (n=8) transfected with the mutant sgk DNA performed similarly to rats(n=8) transfected with a control vector during the visible platform learning test [$F(1,14)=1.05$, $P>0.05$]. No significant difference was found for the first trial, either [$F(1,14)=0.37$, $P>0.05$].

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of determining whether a person is deficient in spatial learning, the method comprising:
    providing a sample from the person, the sample containing an sgk gene product from a hippocampus of the person; and
    determining an expression level of the sgk gene product in the sample;
        wherein the expression level in the sample, if lower than that in a sample containing an sgk gene product from a hippocampus of a normal person, indicates that the person is deficient in spatial learning.

2. The method of claim 1, wherein the sgk gene product is an sgk mRNA.

3. A method of determining whether a test rodent is deficient in spatial learning, the method comprising:
    providing a sample from the test rodent, the sample containing sgk gene product from a hippocampus of the test rodent, and determining an expression level of the sgk gene product in the sample, wherein the expression level in the sample, if lower than that in a sample containing sgk gene product from a hippocampus of a normal rodent of the same species as the test rodent, indicates that the test rodent is deficient in spatial learning.

4. The method of claim 3, wherein the sgk gene product is sgk mRNA.

5. The method of claim 3, wherein the test rodent is a rat.

6. The method of claim 3, wherein the test rodent is a mouse.

7. The method of claim 4, wherein the test rodent is a rat.

8. The method of claim 4, wherein the rodent is a mouse.

* * * * *

SEQUENCE LISTING

<160> NUMBER OF SEQ ID NOS: 12

<210> SEQ ID NO 1
<211> LENGTH: 45
<212> TYPE: DNA
<213> ORGANISM: Artificial Sequence
<220> FEATURE:
<223> OTHER INFORMATION: probe

<400> SEQUENCE: 1
gcggagatcc ctcttagacc tgcatcttcc ttctcactga gacca          45

<210> SEQ ID NO 2
<211> LENGTH: 45
<212> TYPE: DNA
<213> ORGANISM: Artificial Sequence
<220> FEATURE:
<223> OTHER INFORMATION: probe

<400> SEQUENCE: 2
tggtctcagt gagaaggaag atgcaggtct aagagggatc tccgc          45

<210> SEQ ID NO 3
<211> LENGTH: 28
<212> TYPE: DNA
<213> ORGANISM: Artificial Sequence
<220> FEATURE:
<223> OTHER INFORMATION: primer

<400> SEQUENCE: 3
cggaattcac cgtcaaaacc gaggctcg          28

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
gctctagatc agaggaagga gtccatagg          29

<210> SEQ ID NO 5

-continued

```
<211> LENGTH: 28
<212> TYPE: DNA
<213> ORGANISM: Artificial Sequence
<220> FEATURE:
<223> OTHER INFORMATION: primer

<400> SEQUENCE: 5
cggaattcac cgtcaaaacc gaggctcg                                    28

<210> SEQ ID NO 6
<211> LENGTH: 45
<212> TYPE: DNA
<213> ORGANISM: Artificial Sequence
<220> FEATURE:
<223> OTHER INFORMATION: primer

<400> SEQUENCE: 6
gctctagatc agaggaagga gtccatagga ggggcatagg cgaag                 45

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ctctgtgtgc tgaagggggg                                             20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gggacgcagc aacagacatt                                             20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9 tttttttttcc caacccttgc                                            20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aatgaacaaa ggttgggggg                                             20

<210> SEQ ID NO 11
<211> LENGTH: 13
<212> TYPE: DNA
<213> ORGANISM: Artificial Sequence
<220> FEATURE:
<223> OTHER INFORMATION: primer

<400> SEQUENCE: 11
```

-continued

```
aagcttgcgg tga                                              13

<210> SEQ ID NO 12
<211> LENGTH: 16
<212> TYPE: DNA
<213> ORGANISM: Artificial Sequence
<220> FEATURE:
<223> OTHER INFORMATION: primer

<400> SEQUENCE: 12
aagctttttt tttta                                            16
```